United States Patent [19]

Ohno et al.

[11] Patent Number: 5,710,351
[45] Date of Patent: Jan. 20, 1998

[54] PROCESS FOR PRODUCING HEXAFLUOROETHANE

[75] Inventors: Hiromoto Ohno; Tetsuo Nakajo; Tatsuharu Arai; Toshio Ohi, all of Kanagawa, Japan

[73] Assignee: Showa Denko K.K., Tokyo, Japan

[21] Appl. No.: 630,534

[22] Filed: Apr. 10, 1996

[51] Int. Cl.$^6$ .................................. C07C 17/00
[52] U.S. Cl. .................................. 570/123; 570/161
[58] Field of Search .................................. 570/123, 161

[56] References Cited

U.S. PATENT DOCUMENTS

| | | | |
|---|---|---|---|
| 4,281,119 | 7/1981 | Lagow et al. | 544/106 |
| 5,149,744 | 9/1992 | Tarancon | 525/356 |
| 5,585,112 | 12/1996 | Unger et al. | 424/450 |

OTHER PUBLICATIONS

CA 123:68091 (1995).

CA 109:132430 (1988).

*Primary Examiner*—Paul J. Killos
*Attorney, Agent, or Firm*—Sughrue, Mion, Zinn, Macpeak & Seas, PLLC

[57] ABSTRACT

A process for producing hexafluoroethane which comprises reacting a hydrofluorocarbon containing two carbon atoms in the molecule with fluorine gas at an elevated temperature in a vapor phase in the presence of a diluent gas.

10 Claims, No Drawings

PROCESS FOR PRODUCING HEXAFLUOROETHANE

FIELD OF THE INVENTION

The present invention relates to a process for producing hexafluoroethane by reacting a hydrofluorocarbon containing two carbon atoms in the molecule with fluorine gas at an elevated temperature in a vapor phase in the presence of a diluent gas.

BACKGROUND OF THE INVENTION

Hexafluoroethane (hereinafter abbreviated as "FC-116" or "$CF_3CF_3$") is used, for example, for the dry etching of semiconductors.

With respect to the production of FC-116, various methods have hitherto been proposed. Examples of known such methods include (1) an electrolytic fluorination method using ethane and/or ethylene as a starting material; (2) a pyrolytic method in which tetrafluoroethylene or another starting material is pyrolyzed; (3) a method comprising fluorinating acetylene, ethylene, and/or ethane, etc. with a metal fluoride; (4) a method comprising fluorinating dichlorotetrafluoroethane, chloropentafluoroethane, or the like with hydrogen fluoride; and (5) a direct fluorination method in which ethane or the like is reacted with fluorine gas.

Method (1) above is disadvantageous in that many side reactions occur and there are problems concerning the separation and purification of the reaction product.

Method (2) not only necessitates a high reaction temperature, but results in a low yield. Method (3) has problems concerning regeneration with fluorine gas yielded from the metal fluoride, the consumption of fluorine, etc., although the control of the heat of reaction is improved. In method (4), where hydrogen fluoride is used, the reaction yields a large amount of hydrochloric acid as a by-product and necessitates a high temperature, and that the yield is low.

Known examples of the reaction in method (5) include (a) a method in which fluorine gas is reacted with ethane ($C_2H_6$) by means of a jet reactor to obtain tetrafluoromethane and $C_2F_6$, and in which nitrogen is used as a diluent gas (*J. Amer. Chem. Soc.*, 77, 3307 (1955), *J. Amer. Chem. Soc.*, 82, 5827 (1960)); (b) a method in which C—H is fluorinated with fluorine gas by means of a reactor having a porous alumina pipe (EP-31,519 (1981)); and (c) a method in which a linear hydrocarbon is fluorinated with fluorine gas in the presence of a diluent gas by means of a reactor having a porous metal pipe (double-pipe reactor), the diluent gas being $SF_6$, $CF_4$, $C_2F_6$, or $C_3F_8$ (EP-32,210 (1981)).

Other known examples of the reaction using fluorine gas include (e) a method in which fluorine gas is reacted with a saturated or unsaturated hydrocarbon or a partially fluorinated hydrocarbon to produce a hydrofluorocarbon (U.S. Pat. No. 5,406,008 (1995)); and a method in which a fluorinated alkene is produced from an alkene and carbon onto which fluorine gas has been adsorbed (JP-A-2-207052). (The term "JP-A" as used herein means an "unexamined published Japanese patent application.")

The direct fluorination method using fluorine gas as described above has drawbacks that since fluorine gas, which is extremely reactive, is used, there is a danger of explosion of the organic compound as a substrate and fluorine gas and there is a danger of corrosion, etc. In addition, there are a fear of side reactions including the cleavage and polymerization of C—C bonds due to heat generation and a danger of an abrupt reaction or explosion due to the formation and deposition of carbon, etc. For example, in the case of synthesizing a perfluoro compound from a linear hydrocarbon and fluorine gas by the direct fluorination method, the reaction is accompanied by an exceedingly large quantity of heat as shown in schemes (1) and (2).

The reaction shown by scheme (1), in which ethane is used as a starting material, needs 6 mol of fluorine per mol of ethane, while the reaction shown by scheme (2), in which methane is used as a starting material, needs 4 mol of fluorine gas per mol of methane.

Thus, the quantity of heat of reaction is proportional to the number of moles of fluorine; the larger the fluorine amount, the larger the quantity of heat of reaction. The increased heat of reaction tends to cause the cleavage of C—C bonds, explosion, etc., and results in a reduced yield, thus posing problems concerning industrial production and operation. Conventional techniques used for inhibiting the abrupt generation of heat of reaction in the direct fluorination method include: to dilute fluorine with an inert gas (e.g., nitrogen or helium); to dissolve the organic compound as a substrate beforehand into a solvent inert to fluorine to prepare a low-concentration solution; and to conduct the reaction in a low-temperature region. For the reaction conducted in a vapor phase, an apparatus such as, e.g., a jet reactor has been proposed so that fluorine comes into contact with the organic compound as a substrate little by little.

SUMMARY OF THE INVENTION

The present invention has been achieved in order to eliminate the problems described above and to accomplish the subject described above. Accordingly, an object of the present invention is to provide a process by which FC-116 can be safely and efficiently produced at low cost by the direct fluorination method using an organic compound as a substrate and fluorine gas.

Other objects and effects of the present invention will be apparent from the following description.

The present invention provides a process for producing hexafluoroethane which comprises reacting a hydrofluorocarbon (HFC) containing two carbon atoms in the molecule with fluorine gas at an elevated temperature in a vapor phase in the presence of a diluent gas.

DETAILED DESCRIPTION OF THE INVENTION

The diluent gas preferably comprises at least one of tetrafluoromethane, hexafluoroethane, octafluoropropane, and hydrogen fluoride, and is preferably rich in hydrogen fluoride (the hydrogen fluoride content thereof being preferably 50% or higher based on the total amount of the diluent gas).

The organic compound used as a substrate is a hydrofluorocarbon (HFC) containing two carbon atoms in the molecule, and is a compound containing three or more fluorine atoms in the molecule. The substrate is preferably 1,1,1,2-tetrafluoroethane ($CF_3CH_2F$), 1,1,2,2-tetrafluoroethane ($CHF_2CHF_2$), and/or pentafluoroethane, and is preferably 1,1,1,2-tetrafluoroethane.

In carrying out the reaction, the concentration of the hydrofluorocarbon containing two carbon atoms in the molecule as measured at the reactor inlet is preferably regulated to 6 mol % or lower. In the case of 1,1,1,2-tetrafluoroethane, the concentration thereof as measured at the reactor inlet is preferably regulated to 4 mol % or lower.

The reaction is conducted at an elevated temperature, which is preferably in the range of from 250° to 500° C. The reaction is preferably performed at a pressure of from 0 to 3 MPa.

The process for producing FC-116 according to the present invention is explained below in detail.

The organic compound used as a starting material in the present invention, which is a hydrofluorocarbon containing two carbon atoms in the molecule, is represented by formula (3).

$C_2H_xF_y$ (3)

In formula (3), x is an integer of $1 \leq x \leq 5$ and y is an integer of $1 \leq y \leq 5$, provided that x+y=6. Examples of this compound are fluoroethane ($C_2H_5F$), 1,2-difluoroethane ($CH_2FCH_2F$), 1,1-difluoroethane ($CHF_2CH_3$), 1,1,1-trifluoroethane ($CF_3CH_3$), 1,1,2-trifluoroethane ($CHF_2CH_2F$), 1,1,1,2-tetrafluoroethane ($CF_3CH_2F$), 1,1,2,2-tetrafluoroethane ($CHF_2CHF_2$), and pentafluoroethane ($CF_3CHF_2$). These starting materials may be used either alone or as a mixture of two or more thereof.

As stated hereinabove, the reaction of an organic compound with fluorine gas is accompanied by an exceedingly large quantity of heat, and the quantity of heat of reaction is proportional to the number of moles of fluorine, i.e., the larger the fluorine amount, the larger the quantity of heat of reaction. Because of this, the smaller the number of H atoms which should be replaced by F atoms, the easier the control of the heat of reaction and the smaller the use amount of fluorine, which is expensive. Consequently, desirable starting materials among the aforementioned hydrofluorocarbons are the compounds containing three or more fluorine atoms in the molecule. Preferred are the compounds having four or more fluorine atoms, specifically 1,1,1,2-tetrafluoroethane, 1,1,2,2-tetrafluoroethane, and/or pentafluoroethane.

1,1,1,2-Tetrafluoroethane and pentafluoroethane are being industrially produced as substitutes for chlorofluorocarbons (CFC) and hydrochlorofluorocarbons (HCFC). Both are hence easily available, and commercial products thereof have a purity as high as 99.9% or higher. In the case of the production of FC-116 from these compounds and fluorine gas, the heat of reaction is as shown in schemes (4) and (5).

$CF_3CH_2F + 2F_2 \rightarrow CF_3CF_3 + 2HF$ (4)
($\Delta H = -231$ kcal/mol)

$CF_3CHF_2 + F_2 \rightarrow CF_3CF_3 + HF$ (5)
($\Delta H = -119$ kcal/mol)

Thus, the use of 1,1,1,2-tetrafluoroethane or pentafluoroethane as a starting material has an advantage that the quantity of heat of reaction can be as small as about from ⅓ to ⅙ of those in the proportion of FC-116 from hydrocarbon compounds and fluorine gas.

Upon comparing 1,1,1,2-tetrafluoroethane and pentafluoroethane, 1,1,1,2-tetrafluoroethane is preferred. One of the reasons for this is that 1,1,1,2-tetrafluoroethane is more reactive when used as a starting material. The other reason, which is important, is concerned with the purity of the currently industrially produced commercial products of the two compounds. Specifically, commercial products of 1,1,1,2-tetrafluoroethane have a purity of 99.9% or higher, and the impurities contained therein are mostly accounted for by 1,1,2,2-tetrafluoroethane, which is an isomer, and include almost no chlorine compounds.

In contrast, pentafluoroethane forms an azeotropic mixture together with chloropentafluoroethane ($CF_3CClF_2$), so that pentafluoroethane products which have undergone distillation and other purification operations contain chloropentafluoroethane in an amount of from several hundreds to several thousands of ppm. The presence of this chlorine compound during the reaction is undesirable in that it yields chlorine fluoride, chlorine, etc. as by-products. Consequently, 1,1,1,2-tetrafluoroethane is especially useful.

The reaction of the hydrofluorocarbon described above with fluorine gas is conducted at an elevated temperature in the presence of a diluent gas.

Although an inert gas such as nitrogen, helium, or argon is generally employed as a diluent gas, this method is not always advantageous in cost in view of the necessity of separation of the inert gas from the objective compound and purification thereof. In a preferred embodiment of the present invention, a gas comprising at least one of tetrafluoromethane (boiling point: −127.9° C.), hexafluoroethane (boiling point: −78.5° C.), octafluoropropane (boiling point: −37.7° C.), and hydrogen fluoride (boiling point: 20° C.) is used as the diluent gas. These diluent compounds not only have the effect of inhibiting combustion, explosion, etc., but also are advantageous in energy cost for separation and purification because they have a higher boiling point than helium (boiling point: −268.9° C.) and other diluent gases. It is especially preferred to use a diluent gas rich in hydrogen fluoride (the hydrogen fluoride content thereof being preferably 50% or higher based on the total amount of the diluent gas).

For example, the reaction between 1 mol of 1,1,1,2-tetrafluoroethane and 2 mol of fluorine yields 1 mol of FC-116 and 2 mol of hydrogen fluoride, as shown by scheme (4). Since the difference in boiling point between the objective compound, i.e., FC-116, and the by-product, i.e., hydrogen fluoride, is about 100° C., a gas rich in hydrogen fluoride can be obtained by a simple method such as, e.g., partial condensation. Use of this gas as a diluent gas is economical. Alternatively, hydrogen fluoride may be newly added as a diluent gas. In the direct fluorination method in which fluorine gas is used, carbon formation, deposition, etc. occur as a result of, e.g., C—C bond cleavage during the long-term reaction as stated hereinabove. Although the carbon formation, deposition, etc. may cause a danger of an abrupt reaction with fluorine gas or explosion, the use of hydrogen fluoride as a diluent gas is effective in inhibiting the formation and deposition of carbon. The term "rich in hydrogen fluoride" means "containing hydrogen fluoride as a major component."

The reaction of a reaction substrate with fluorine gas is conducted in the presence of a diluent gas. Before being introduced into a reactor, either or both of the reaction substrate and fluorine gas are generally diluted with the diluent gas. From the standpoint of safety, both the reaction substrate and the fluorine gas are preferably diluted with the diluent gas in a sufficiently low concentration.

Reaction temperature is among the conditions which should be taken in account in order to efficiently carry out the reaction of the starting material, i.e., a hydrofluorocarbon of the kind described above, with fluorine gas in the presence of a diluent gas such as those described above. The optimum range of reaction temperature varies depending on the contact time and the kind of the hydrofluorocarbon as a starting material. For example, in the case where the reaction of 1,1,1,2-tetrafluoroethane with fluorine is conducted using a long contact time (15 seconds), the reaction begins at a reaction temperature of about 50° C. and the conversion reaches about 100% at a temperature of about 250° C. An elevated reaction temperature is used, preferably in the range of from 250° to 500° C.

Reaction temperatures lower than 250° C. are undesirable in that the conversion of the hydrofluorocarbon is low. Reaction temperatures exceeding 500° C. are not preferred in, for example, that C—C bond cleavage, polymerization, etc. occur to result in a reduced yield, and that there are problems such as reactor corrosion and an increased energy cost.

Although the contact time is not particularly limited, it is in the range of, for example, from 0.1 to 120 seconds. In general, however, the contact time is desirably from 1 to 30 seconds, preferably from 3 to 30 seconds, since longer contact times necessitate a larger reactor and are hence uneconomical. It is preferred to well mix the reaction substrate with the fluorine gas.

As stated hereinabove, in the direct fluorination method in which fluorine gas is used, there is the danger that the organic compound as a substrate (in particular a compound containing hydrogen) may burn or explode upon exposure to fluorine, because fluorine is extremely reactive.

In the reaction of the present invention, it is important that since a hydrofluorocarbon, containing hydrogen, is used as the organic compound substrate, the explosion of the hydrofluorocarbon and fluorine should be prevented. For preventing explosion, the mixed gas should be regulated so as to have a composition outside the explosion range therefor. As a result of investigations made by the present inventors on the explosion ranges for mixtures of hydrofluorocarbons with fluorine gas, the lower limit of the explosion range for pentafluoroethane was found to be a concentration of about 6 mol %, and that for 1,1,1,2-tetrafluoroethane was found to be a concentration of about 4%. It is preferred that the concentration of the hydrofluorocarbons of the present invention as measured at the reactor inlet be regulated so as to be within the respective safety ranges therefor.

The molar ratio of the fluorine gas to the hydrofluorocarbon both fed to the reaction system is preferably from 0.5 to 5.0, more preferably from 1.0 to 3.0. If the molar proportion of the fluorine gas fed is below 0.5, the reaction does not proceed efficiently. Molar proportions thereof exceeding 5.0 are uneconomical in that fluorine gas is fed in excess and this necessitates, for example, an apparatus for the recovery thereof.

In carrying out the reaction, the reaction pressure is also important from the standpoint of preventing dangers such as explosion. In general, the higher the pressure, the wider the explosion range. Consequently, the reaction is conducted desirably at a lower pressure, preferably in the range of from 0 to 3 MPa.

The reactor is preferably made of a material having resistance to corrosive gases. Examples of the material include nickel, Inconel, and Hastelloy.

The following are Examples of the present invention, but the invention should not be construed as being limited thereto.

The starting materials used in the following reactions are shown below first.

(1,1,1,2-Tetrafluoroethane)

Ecoloace 134a (trade name), which is currently being supplied as a substitute for CFC-12 ($CCl_2F_2$), was used. It had a purity of 99.99% or higher, and contained 1,1,2,2-tetrafluoroethane, an isomer, in an amount of about 20 ppm. No chlorine compound was detected therein.

(Pentafluoroethane)

Ecoloace 125 (trade name), which is currently being supplied as a substitute for HCFC-22 ($CHClF_2$), was used. It had a purity of 99.95% or higher, and contained, as impurities, 1,1,1,2-tetrafluoroethane, 1,1,1-trifluoroethane, and chlorine compounds, i.e., chloropentafluoroethane and 1-chloro-1,2,2,2-tetrafluoroethane.

EXAMPLE 1

An Inconel 600 reactor having an inner diameter of 20.6 mm and a length of 500 mm (electrical heating type; the reactor had undergone a passivation treatment with fluorine gas at 600° C.) was heated to 280° C. while introducing nitrogen gas as a diluent gas thereinto at a rate of 30 NL/h. Subsequently, hydrogen fluoride was introduced thereinto as a diluent gas at a rate of 50 NL/h. The flow of the diluent gas was divided into two, to one of which was added 1,1,1,2-tetrafluoroethane as a hydrofluorocarbon at a rate of 1.8 NL/h. Thereafter, fluorine gas was fed by adding the same to the other of the divided diluent gas flows at a rate of 3.9 NL/h to conduct a reaction.

The concentration of 1,1,1,2-tetrafluoroethane as measured at the reactor inlet was 2.1 mol %, and the reaction temperature was 280° C.

Three hours after, the gaseous mixture resulting from the reaction was treated with aqueous potassium hydroxide solution and aqueous potassium iodide solution to remove the hydrogen fluoride and the unreacted fluorine gas. The residual gas was analyzed for composition by gas chromatography. As a result, the gas composition (vol %) was found to be as follows.

| | |
|---|---|
| $CF_4$ | 0.56% |
| $C_2F_6$ | 84.59% |
| $CF_3CHF_2$ | 14.45% |
| $CF_3CH_2F$ | trace |
| Others | 0.40% |

EXAMPLES 2 TO 5

Reaction was carried out under the same conditions as in Example 1, except that the reaction temperature was varied. The reaction temperatures used and the results obtained are shown in Table 1.

TABLE 1

| Example | Reaction temperature (°C.) | Compositon (vol %) | | | | |
|---|---|---|---|---|---|---|
| | | FC-14 | FC-116 | HFC-125 | HFC-134a | Others |
| 2 | 200 | 0.49 | 65.16 | 28.85 | 5.20 | 0.3 |
| 3 | 350 | 0.78 | 90.52 | 8.02 | — | 0.68 |
| 4 | 450 | 1.28 | 95.17 | 2.66 | — | 0.89 |
| 5 | 550 | 4.68 | 92.55 | 0.89 | — | 1.88 |

In the table, FC-14 means $CF_4$, FC-116 means $CF_3CF_3$, HFC-125 means $CF_3CHF_2$, and HFC-134a means $CF_3CH_2F$.

The "Others" in Table 1 consisted mainly of $CO_2$. At 550° C. however formation of $C_3F_8$ was observed. The results show that the yield of the objective compound, FC-116, was low at low temperatures, while at a high temperature of 550° C., the selectivity for the objective compound was low and formation of a $C_3$ perfluoro compound was observed, which was yielded by accelerated C—C bond cleavage and polymerization.

EXAMPLES 6 TO 8

Using the same reactor as in Example 1, reaction was carried out in the same manner as in Example 1, except that pentafluoroethane as a hydrofluorocarbon and fluorine gas were fed at rates of 3.6 NL/h and 3.9 NL/h, respectively, and hydrogen fluoride and nitrogen gas were introduced as diluent gases at rates of 50 NL/h and 30 NL/h, respectively, and that the reaction temperature was varied. The reaction temperatures used and the results obtained are shown in Table 2.

TABLE 2

| Example | Reaction temperature (°C.) | Compositon (vol %) | | | | |
|---|---|---|---|---|---|---|
| | | FC-14 | FC-116 | HFC-125 | Cl compounds | Others |
| 6 | 200 | 0.21 | 6.70 | 92.17 | 0.48 | 0.44 |
| 7 | 300 | 0.48 | 85.21 | 13.07 | 0.47 | 0.77 |
| 8 | 400 | 0.72 | 98.18 | — | 0.22 | 0.88 |

The "Others" in Table 2 consisted mostly of $CO_2$, and the "Cl compounds" consisted mainly of chloropentafluoroethane and 1-chloro-1,2,2,2-tetrafluoroethane.

The results show that although pentafluoroethane was less reactive with fluorine gas than 1,1,1,2-tetrafluoroethane (in a low-temperature region), it gave FC-116 in good yield. However, chlorine and chlorine fluoride were detected in Example 8.

EXAMPLE 9

Using the same reactor as in Example 1, reaction was carried out in the same manner as in Example 1, except that 1,1,1,2-tetrafluoroethane as a hydrofluorocarbon and fluorine gas were fed at rates of 2.2 NL/h and 4.8 NL/h, respectively, and hydrogen fluoride and tetrafluoromethane were introduced at rates of 60 NL/h and 20 NL/h, respectively, and that the reaction temperature was changed to 480° C. The results (vol %) obtained are shown below.

| | |
|---|---|
| $CF_4$ | 1.46% |
| $C_2F_6$ | 95.98% |
| $CF_3CHF_2$ | 1.78% |
| $CF_3CH_2F$ | — |
| Others | 0.78% |

The reaction was continuously performed for 30 days under the conditions described above, and the gas collected at the reactor outlet at the 30th day was analyzed for composition. The results thus obtained were almost the same as the above. Thereafter, the reaction was terminated, and the reactor was cooled to room temperature while introducing nitrogen gas thereinto. The inner surface of the reactor was then examined with a fiber scope (endoscope). As a result, no deposit of carbon or another substance was observed.

According to the process of the present invention, FC-116 can be industrially and safely produced in high yield by reacting a hydrofluorocarbon containing two carbon atoms in the molecule with fluorine gas in a vapor phase in the presence of a diluent gas.

While the invention has been described in detail and with reference to specific embodiments thereof, it will be apparent to one skilled in the art that various changes and modifications can be made therein without departing from the spirit and scope thereof.

We claim:

1. A process for producing hexafluoroethane which comprises reacting a hydrofluorocarbon containing two carbon atoms in the molecule with fluorine gas at an elevated temperature in a vapor phase in the presence of a diluent gas.

2. The process as claimed in claim 1, wherein the diluent gas is a gas comprising at least one of tetrafluoromethane, hexafluoroethane, octafluoropropane, and hydrogen fluoride.

3. The process as claimed in claim 1, wherein the diluent gas is rich in hydrogen fluoride.

4. The process as claimed in claim 1, wherein the reaction is conducted at a temperature of from 250° to 500° C.

5. The process as claimed in claim 1, wherein the hydrofluorocarbon containing two carbon atoms in the molecule is a hydrofluorocarbon containing three or more fluorine atoms.

6. The process as claimed in claim 5, wherein the hydrofluorocarbon containing two carbon atoms in the molecule is at least one of 1,1,1,2-tetrafluoroethane, 1,1,2,2-tetrafluoroethane, and pentafluoroethane.

7. The process as claimed in claim 6, wherein the hydrofluorocarbon containing two carbon atoms in the molecule is 1,1,1,2-tetrafluoroethane.

8. The process as claimed in claim 1, wherein the reaction is conducted while regulating the concentration of the hydrofluorocarbon containing two carbon atoms in the molecule as measured at the reactor inlet to 6 mol % or lower.

9. The process as claimed in claim 8, wherein the concentration of 1,1,1,2-tetrafluoroethane as measured at the reactor inlet is 4 mol % or lower.

10. The process as claimed in claim 1, wherein the reaction is conducted at a reaction pressure of from 0 to 3 MPa.

* * * * *